United States Patent [19]

Elliott

[11] 4,025,510

[45] May 24, 1977

[54] 2,4-DIARYL[1,3,4H]THIADIAZINES FUSED TO QUINOXALINES

[75] Inventor: Arthur John Elliott, New Castle, Del.

[73] Assignee: E. I. Du Pont de Nemours and Company, Wilmington, Del.

[22] Filed: Dec. 1, 1975

[21] Appl. No.: 636,792

[52] U.S. Cl. .............................. 260/243 R; 8/179
[51] Int. Cl.² ...................................... C07D 285/22
[58] Field of Search ............................ 260/243 R

[56] References Cited

UNITED STATES PATENTS 3,954,984   5/1976   Albrecht ........................ 260/243

OTHER PUBLICATIONS

Barnish et al., *J. Chem. Soc.* (C) 1970, pp. 854–859.
McDonald et al., *Chemical Communications* (1969) pp. 392–393.
Barnish et al., *J. Chem. Soc.*, (Perkin I) 1974, pp. 215–219.
Elliott, McMaster University Thesis (1971) selected pages submitted by applicant.

*Primary Examiner*—John M. Ford

[57] ABSTRACT

Compounds are provided which have the formula:

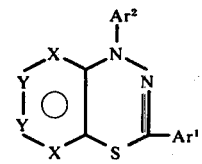

where $Ar^1$ and $Ar^2$ are aromatic radicals and X and Y are 1 to 2 nitrogen atoms and conversely 3 to 2 carbon atoms which may have selected substitutes. Preferably, 2 adjacent carbon atoms (usually the 2 Y's) have a butadienyl or a substituted butadienyl attached thereto. The compounds are useful as dyes.

15 Claims, No Drawings

2,4-DIARYL[1,3,4H]THIADIAZINES FUSED TO QUINOXALINES

BACKGROUND OF THE INVENTION

1. Field of the Invention

This invention relates to thiadiazines and more particularly to new 1,3,4-thiadiazines having aromatic groups at the 2- and 4-positions and a 6-membered nitrogen-containing aromatic ring fused to the 5,6-positions. These new compounds are useful as dyes.

2. Prior Art

A fused-ring system containing the 1,3,4-thiadiazine ring has been prepared by reaction of α-halo-benzaldehyde-2, 4-dihalogenophenylhydrazones and a thioacetate [Barnish, J. Chem. Soc. (C) 1970 854]. These have the structure:

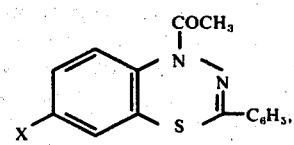

X being Br, Cl or F.

A purple compound having a phenylazo group in the 2-position, i.e.,

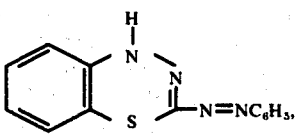

has been reported by McDonald, Chem. Communications 1969. 392. It was prepared from dithizone by oxidation.

Elliott (the applicant), McMaster University Thesis (1971), reacted dithizone with 2,3-dichloroquinozaline to give

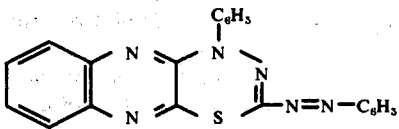

Reaction of dithizone with 2-chloro-3-nitropyridine gave the purple compound of the structure

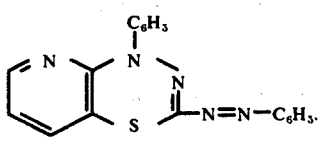

The azo compounds lack fluorescence and have poor dye quality.

Compounds having aromatic nuclei directly attached to both the 2- and 4-positions of a 1,3,4-thiadiazine ring have been reported, but the 5,6-positions were not attached to a heterocyclic aromatic ring.

SUMMARY OF THE INVENTION

According to the present invention there is provided 1,3,4-thiadiazines which have attached to the 2- and 4-positions aromatic radicals and fused to the 5- and 6-positions of the thiadiazine ring a 6-membered aromatic ring containing 1 to 2 nuclear nitrogens. The compounds have the general formula:

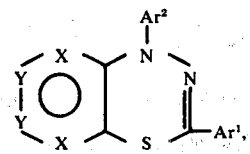

wherein
Ar$^1$ represents an aromatic monovalent radical of up to 10 nuclear atoms including those having up to 2 heteroatoms (oxygen, nitrogen, and/or sulfur);
Ar$^2$ is an aromatic monovalent radical of up to 10 carbons and is a 6–10 carbon aryl, pyridazinyl, pyrimidinyl, pyrazinyl, furyl, thienyl, pyrrolyl, thiazolyl, oxazolyl, imidazolyl, indolyl, 3- or 4-pyridinyl, 3-, 4-, 5-, 6- or 7-quinolinyl, 4-, 5-, 6-, 7- or 8-isoquinolinyl, or a 5-, 6- or 7-benzothiazolyl;
X and Y represent 1 to 2 nitrogen atoms and conversely 3 to 2 nuclear carbons, the latter of which can have halogen (F,Cl,Br), nitro, methoxy, methylthio, sulfonamido, cyano, carboxy, carbamyl, alkyl, carbalkoxy, sulfamyl, sulfonyl, phenyloxysulfonyl, acylamino, alkoxyalkylsulfamyl, alkoxyalkylcarbamyl, (di)alkylcarbamyl, (di)alkylsulfamyl, and dialkylamino attached to up to 2 nuclear carbons, where each alkyl is from 1–4 carbon atoms, and optionally attached to adjacent carbons a butadienyl or butadienyl having the latter substituents, the circle representing aromatic unsaturation. Ar$^1$ and Ar$^2$ can have up to 2 substituents which can be cyano, chloro, bromo, nitro, methoxy, methylthio, hydroxy, dialkylamino, dialkylsulfonamido, alkyl or acylamino substitutents of up to 4 carbons each.

A preferred class of compounds for the purpose of this invention are those of the formula

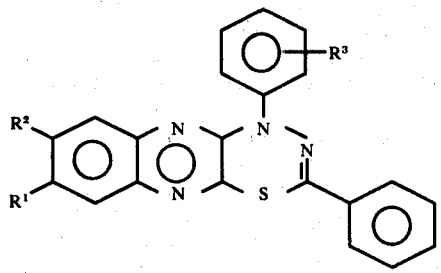

wherein
R$^1$ is —H, —Cl, —NO$_2$, —CH$_3$, alkoxyalkylcarbamyl, carbalkoxy, (di)alkylcarbamyl, sulfamyl, (di)alkylsulfamyl, alkoxyalkylsulfamyl or phenyloxysulfonyl;
R$^2$ is —H or —CH$_3$; and
R$^3$ is —H, —Cl, —Br, —NO$_2$, —CH$_3$ or —OCH$_3$.

Also provided is a process for the preparation of these compounds by reaction of a thioaroyl arylhydrazine,

with a vicinyl halo or halonitro heterocyclic aromatic compound containing 1 to 2 nuclear nitrogens as represented by the structure

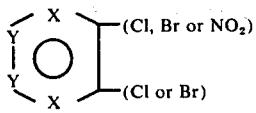

wherein the X and Y groups are as defined above.

DETAILED DESCRIPTION OF THE INVENTION

The thioaroyl arylhydrazines used as a starting reactant are readily obtained from arylhydrazines by thioaroylation with a reagent such as a thioaroyl halide (Ar$^1$CSX where X = Cl or Br). Mono- and dithiocarboxylic acids (Ar$^1$CSOR and Ar$^1$CSSR) are very useful, e.g., thioaroylthioacetic acid (Ar$^1$CSSCH$_2$COOH) is generally preferred to give thioaroyl arylhydrazines for the process of this invention. The preparation of these compounds has been disclosed in the literature, e.g., Jensen et al., Acta Chim Scand, 15, 1087 (1961).

The thioaroyl arylhydrazines thus obtainable can be represented by the formula

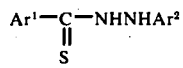

where Ar$^1$ and Ar$^2$ represent aromatic monovalent radicals of up to 10 nuclear atoms each and may have up to 2 heteroatoms (oxygen, nitrogen, sulfur). These include for Ar$^1$ rings of 5 or 6 nuclear atoms such as 6–10 carbon aryl (phenyl, tolyl, xylyl, tetramethylphenyl, and naphthyl), 6 nuclear atom heteroaryl (pyridinyl, 3-methylpyridinyl, quinolinyl and isoquinolinyl, pyridazinyl, and pyrimidinyl), 5-nuclear atom heteroaryl (furyl, thienyl, pyrrolyl, thiazolyl, oxazolyl, pyrazinyl, pyrazolyl, imidazolyl, indolyl, and benzothiazolyl). Ar$^2$ in the hydrazines is a 6–10 carbon aryl, 3- or 4-pyridinyl, 3-, 4-, 5-, 6- or 7-quinolinyl, 4-, 5-, 6-, 7- or 8-isoquinolinyl, 5-, 6- or 7-benzothiazolyl, pyridazinyl, pyrimidinyl, pyrazinyl, furyl, thienyl, pyrrolyl, thiazolyl, oxazolyl, imidazolyl and indolyl.

It is noted that certain position isomers of selected heterocyclic aromatic radicals cannot be present in Ar$^2$ (e.g., 2-pyridinyl, 2- or 4-benzothiazolyl, 2-or 8-quinolinyl and 1- or 3-isoquinolinyl) because the thioaroyl arylhydrazines are unstable and undergo cyclization to give benzotriazoles. Thus the Ar$^2$ is selected such that the thioaroyl arylhydrazine is relatively stable (i.e., does not undergo an internal ring formation for the preparation of the thiadiazines of the invention).

These thioaroyl aromatic hydrazines react with vicinal halo or halonitro heterocyclic compounds containing 6 nuclear atoms and 1 or 2 nitrogens. Such compounds have the general structure

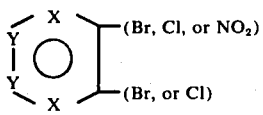

wherein 1 or 2 of the X and Y groups is N, the remainder being nuclear carbon, to the latter (carbon) being attached —H, or up to a total of two lower alkyl (1–4 carbon), halo, (bromo, chloro and fluoro), nitro, lower alkylthio or lower alkoxy such as methylthio or methoxy, carboxy (including cyano, carboxylic acid, carbonyl, or lower alkyl carbalkoxy), sulfamyl, sulfonyl, carbamyl, acylamino, dialkylamino, alkoxyalkylsulfamyl, alkoxyalkylcarbamyl, phenyloxysulfonyl, (di)alkylcarbamyl, (di)alkylsulfamyl, or sulfonamido substituents. Adjacent carbons can also bear a butadienyl group (—CH=CH—CH=CH—) or a butadienyl group having one to two hydrogen replaced by the above groups, preferably, the —Cl, —NO$_2$, —CH$_3$, alkoxyalkylcarbamyl, carbalkoxy, (di)alkylcarbamyl, sulfamyl, (di)alkylsulfamyl, alkoxyalkylsulfamyl or phenyloxysulfonyl groups such as in:

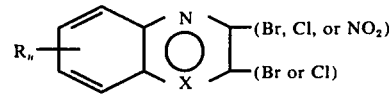

where X is CH or N, R represents at least one of the above named substituents with $n$ being 0, 1 or 2.

The reaction of the thioaroyl arylhydrazines with the vicinal halo or halonitro heterocycle to give the new 1,3,4-thiadiazines is an equimolar one and it is preferred the starting materials be present initially in substantially equimolar ratio. The reaction takes place in liquid phase and nonreactive polar solvent, particularly with an alcohol, a nitrile or a disubstituted (e.g., lower alkyl) amide. Lower nitriles and amides are preferred, e.g., acetonitrile, propionitrile, dimethylformamide or diethylformamide. While it is preferred that a water-soluble solvent be used since the new thiadiazines can be removed and purified by dilution of the solvent with water, water-immiscible organic solvents such as aromatic hydrocarbon solvents of 6 to 9 carbons, e.g., xylene, toluene, can be used. The reaction temperature is generally from about 20°–100° C, although higher temperatures can be used. The reaction time is not critical; usually a few minutes to an hour is sufficient for the reaction. Since the reaction involves the removal of an acid (HCl, HBr or HNO$_2$), it is preferred that the acid formed be removed by combination with a basic absorber such as a lower alkyl tertiaryamine, e.g., trimethyl- or triethylamine. The new compounds are readily separated and purified from the components of the reaction mixture.

The preferred compounds of the invention, i.e., those of formula I, are prepared by reaction of the appropriate thiobenzoylarylhydrazine (II)

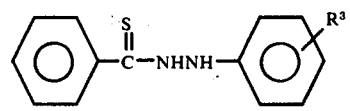

with a 2,3-dichloroquinoxaline (III)

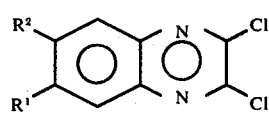

wherein R$^1$, R$^2$ and R$^3$ are as defined above, in acetonitrile and triethylamine.

Isomeric products may result in the reaction, particularly when unsymmetrical vicinal halo or nitro halo heterocyclic intermediates are used. In the examples, which follow, products (including isomers) that result are illustrated. Temperatures are in °C.

EXAMPLE 1

2,4-Diphenyl-4H-quinoxalino[2,3-e][1,3,4]thiadiazine

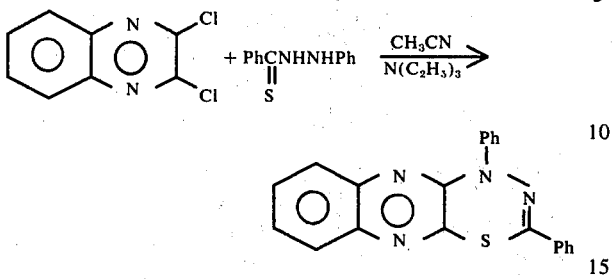

N-thiobenzoyl-N'-phenylhydrazine (2.28 g), 2,3-dichloroquinoxaline (1.99 g), acetonitrile (70 ml) and triethylamine (10 ml) were refluxed together for 30 min, and allowed to cool. The yellow solid was filtered off, washed well with water and dried. The yield was 2.5 g (72%) of yellow needles, mp, 196°, of the quinoxalinothiadiazine. Nmr spectrum: (in CF$_3$COOH): multiplets at δ 7.2–8.0. Mass spectrum: M+ measured 354.0986; Calcd. for C$_{21}$H$_{14}$N$_4$S: 354.0938.

Anal. Calcd. for C$_{21}$H$_{14}$N$_4$S: C, 71.17; H, 3.98; N, 15.81. Found: C, 70.85; H, 4.26; N, 16.10.

A further preparation gave the purified compound of mp 203°–205° which dyed polyester fabric a greenish-yellow.

EXAMPLE 2

6,7-Dicyano-2,4-diphenyl-4H-pyrazino[2,3-e][1,3,4]thiadiazine

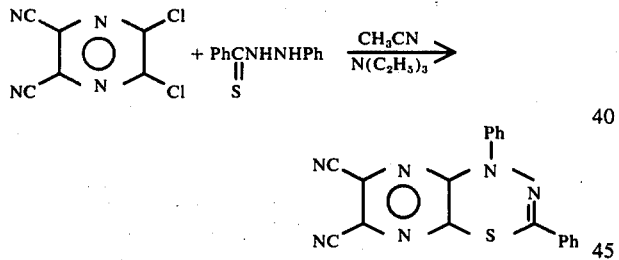

N-Thiobenzoyl-N'-phenylhydrazine (2.28 g), dichlorodicyanopyrazine (1.99 g) and acetonitrile (70 ml) were stirred together at room temperature and triethylamine (10 ml) was added. There was an immediate reaction and a red solid precipitated. Stirring was continued for 30 min, and the product was filtered off, washed well with water and dried. The pyrazinothiadiazine, 2.9 g (83%) was obtained as red needles, mp 246°. Mass spectrum: M+ measured 354.0698; Calcd for C$_{19}$H$_{10}$N$_6$S: 354.0687.

Anal. Calcd for C$_{19}$H$_{10}$N$_6$S: C, 64.40; H, 2.84; N, 23.71 Found: C, 64.20; H, 3.22; N, 23.92

EXAMPLE 3

Reaction of 5-Bromo-4-chloro-2-methylthiopyrimidine and N-Thiobenzoyl-N'-phenylhydrazine

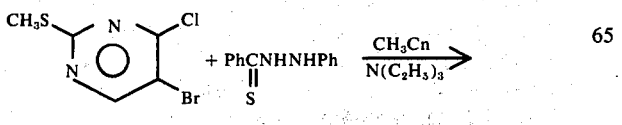

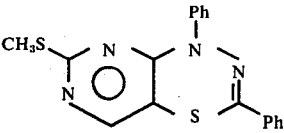

2,4-Diphenyl-6-methylthio-4H-pyrimidino[4,5-e][1,3,4]thiadiazine and/or

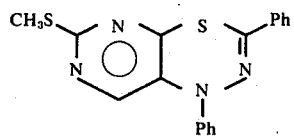

2,4-Diphenyl-7-methylthio-4H-pyrimidino[5,4-e][1,3,4]thiadiazine

N-Thiobenzoyl-N'-phenylhydrazine (2.28 g), 5-bromo-4-chloro-2-methylthiopyrimidine (2.39 g), acetonitrile (70 ml) and triethylamine (10 ml) were boiled together under reflux for 45 min., and then allowed to cool. The yellow solid was filtered off, washed well with water and dried. The pyrimidinothiadiazine, 2.3 g (66%) was obtained as yellow needles, mp 126°. Nmr (in CF$_3$COOH): δ 2.28 (s, 3H), δ 7.3–8.0 (m, 11H). Mass spectrum: M+ measured 350.0659. Calcd. for C$_{18}$H$_{14}$N$_4$S$_2$: 350.0659.

Anal. Calcd. for C$_{18}$H$_{14}$N$_4$S$_2$: C, 61.69; H, 4.03; N, 15.99 Found: C, 61.45; H, 4.11; N, 16.08.

EXAMPLE 4

Reaction of 2-Chloro-3-nitropyridine and N-Thiobenzoyl-N'-phenylhydrazine

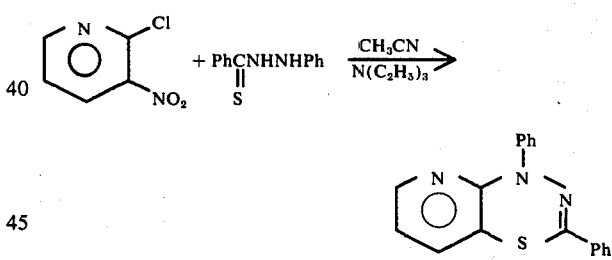

2,4-Diphenyl-4H-pyridino[2,3-e][1,3,4]-thiadiazine and/or

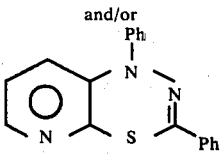

2,4-Diphenyl-4H-pyridino[3,2-e][1,3,4-]-thiadiazine

N-Thiobenzoyl-N'-phenylhydrazine (2.28 g), 2-chloro-3-nitropyridine (1.58g), acetonitrile (70 ml) and triethylamine (10 ml) were boiled together under reflux for 40 min. Water (10 ml) was added and the solution was allowed to cool. The yellow solid was filtered off, washed well with water and dried. The pyridinothiadiazine, 2.3 g (70%) was obtained as yellow needles, mp 99°–100°.

Anal. Calcd. for C$_{18}$H$_{13}$N$_3$S: C, 71.26; H, 4.32; N, 13.85. Found: C, 70.85, H, 4.30; N, 13.62.

EXAMPLE 5

Reaction of 3,4,5-Trichloropyridazine
and N-Thiobenzoyl-N'-phenylhydrazine

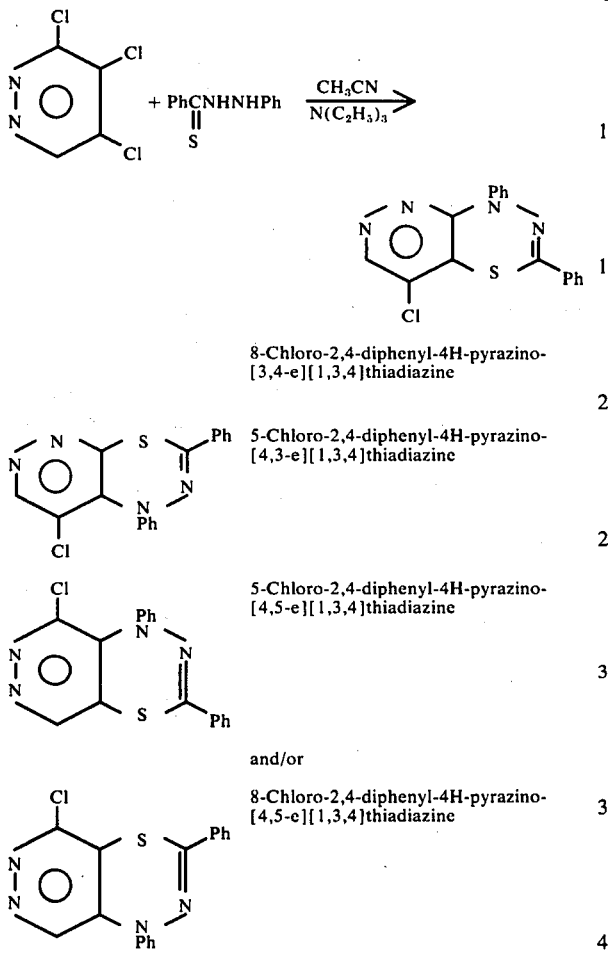

8-Chloro-2,4-diphenyl-4H-pyrazino-
[3,4-e][1,3,4]thiadiazine

5-Chloro-2,4-diphenyl-4H-pyrazino-
[4,3-e][1,3,4]thiadiazine

5-Chloro-2,4-diphenyl-4H-pyrazino-
[4,5-e][1,3,4]thiadiazine and/or

8-Chloro-2,4-diphenyl-4H-pyrazino-
[4,5-e][1,3,4]thiadiazine 3,4,5-Trichloropyridazine (1.83 g), N-thiobenzoyl-N'-phenylhydrazine (2.28 g) and acetonitrile (70 ml) were stirred together at room temperature and triethylamine (10 ml) was added. The mixture was stirred for one hour and water (150 ml) was added. The yellow-orange solid was filtered off, washed well with water and dried. The pyridazinothiadiazine, 2.1 g (62%), was obtained as needles, mp 130°–1°.

Anal. Calcd. for $C_{17}H_{11}N_4SCl$: C, 60.27; H, 3.27; N, 16.54. Found: C, 60.03; H, 3.48; N, 16.69.

EXAMPLE 6

Reaction of 2,3,6-Trichloroquinoxaline
and N-Thiobenzoyl-N'-phenylhydrazine

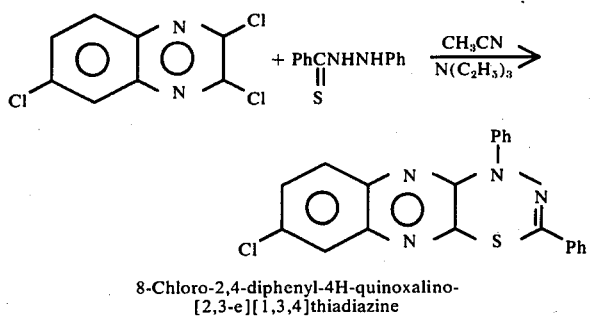

8-Chloro-2,4-diphenyl-4H-quinoxalino-
[2,3-e][1,3,4]thiadiazine and/or

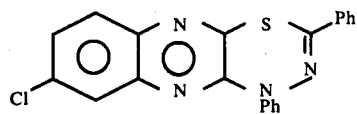

7-Chloro-2,4-diphenyl-4H-quinoxalino-
[2,3-e][1,3,4]thiadiazine

N-Thiobenzoyl-N'-phenylhydrazine (2.28 g), 2,3,6-trichloroquinoxaline (2.33 g), acetonitrile (70 ml) and triethylamine (10 ml) were refluxed for 30 min. The mixture was allowed to cool and the solid was filtered off, washed well with water and dried. Crystallization from acetonitrile gave yellow-orange needles, mp 175°–7° of the quinoxalinothiadiazine, 1.9 g (50%); $\gamma$max, 420m $\mu$ and $a_{max}$33 liters/g$^{-1}$cm$^{-1}$.

Anal. Calcd. for $C_{21}H_{13}N_4SCl$: C, 64.86; H, 3.37; N, 14.41. Found: C, 64.73; H, 3.34; N, 14.16.

EXAMPLE 7

Reaction of 2,3,6-Trichloroquinoxaline
with N-Thiobenzoyl-N'-(2,5-dichlorophenyl)hydrazine

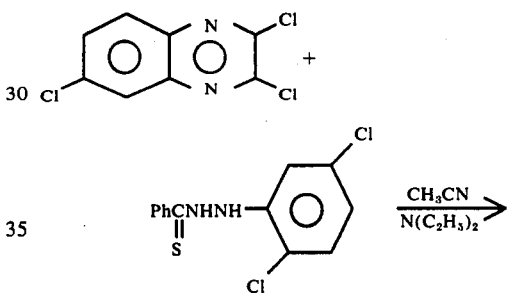

8-Chloro-4-(2,5-dichlorophenyl)-2-
phenyl-4H-quinoxalino
[2,3-e][1,3,4]thiadiazine and/or

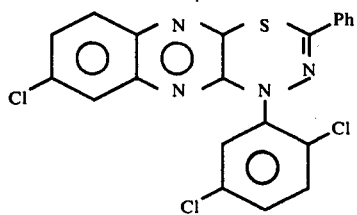

7-Chloro-4-(2,5-dichlorophenyl)-2-
phenyl-4H-quinoxalino
[2,3-e][1,3,4]thiadiazine 2,3,6-Trichloroquinoxaline (2.33 g), N-thiobenzoyl-N'-(2,5-dichlorophenyl)hydrazine (2.97 g), acetonitrile (500 ml) and triethylamine (20 ml) were boiled together under reflux for 2 hrs., and allowed to cool. The solid was filtered off, washed with a little acetonitrile, much water and then dried. The quinoxalino-thiadiazine (3.0 g, 65%) was obtained as bright yellow needles, mp 189°–193°.

Anal. Calcd. for $C_{21}H_{11}N_4SCl_3$: C, 55.10; H, 2.42; N, 12.24. Found: C, 54.92; H, 2.45; N, 12.11.

EXAMPLE 8

4-(2,5-Dichlorophenyl)-6,7-dicyano-2-phenyl-4H-pyrazino[2,3-e][1,3,4]thiadiazine

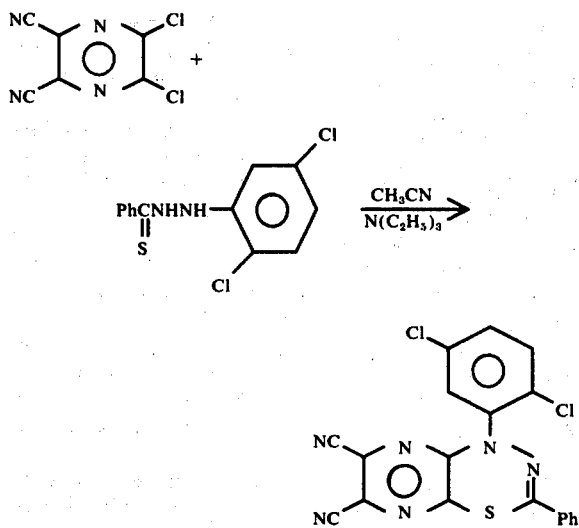

Dichlorodicyanopyrazine (0.99 g), N-thiobenzoyl-N'-(2,5-dichlorophenyl)hydrazine (1.48 g) and acetonitrile (30 ml) were stirred together at room temperature and triethylamine (5 ml) was added. The mixture was stirred for 5 min, and then water (10 ml) was added. The solid was filtered off, washed well with water and crystallized from acetonitrile. The pyrazinothiadiazine, 1.2 g (56%) was obtained as orange needles, mp, 233°–4°.

Anal. Calcd. for $C_{19}H_8N_6SCl_2$: C, 53.92; H, 1.89; N, 19.82. Found: C, 53.66, 54.09; H, 1.79, 1.92, N, 19.71, 20.00.

EXAMPLE 9

4-(7-Chloro-4-quinolyl)-2-phenyl-4H-quinoxalino-[2,3-e][1,3,4]thiadiazine

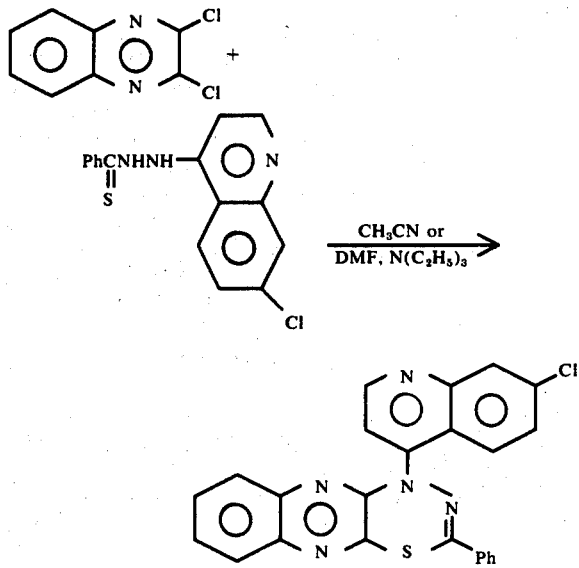

a. In Acetonitrile 2,3-Dichloroquinoxaline (1.99 g), N-thiobenzoyl-N'-(7-chloro-4-quinolyl)hydrazine, acetonitrile (100 ml) and triethylamine (10 ml) were refluxed together for 45 min and cooled. The solid was filtered, washed with water and dried. The quinoxalinothiadiazine (0.31 g, 7%) was obtained as yellow needles, mp 280°.

Anal. Calcd. for $C_{24}H_{14}N_5SCl$: C, 65.53; H, 3.21; N, 15.92. Found: C, 65.00, 64.99; H, 3.19 3.15; N, 15.62, 15.55.

b. In DMF

Experiment repeated with equivalnet amounts of starting material using N,N-dimethyl formamide (DMF) (50 ml) and triethylamine (10 ml). The mixture was refluxed for 40 min and allowed to cool. The solid was filtered off, washed well with water and dried. The quinoxalinothiadiazine, 1.52 g (35%), was obtained as yellow needles, mp 280°.

Anal: Found C, 64.85; H, 3.28; N, 15.79.

Mass spectrum: M+ measured 439.0618. Calcd. for $C_{24}H_{14}ClN_5S$: 439.0657.

When 2-chloro-3-nitroquinoline is used in place of 2-chloro-3-nitropyridine in the general procedure of Example 4, the resulting compound will have the structure

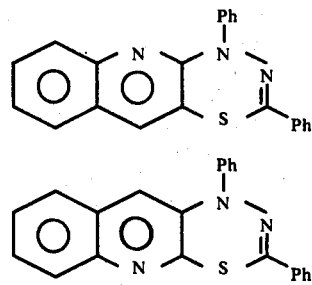

which can be named as 2,4-diphenyl-4H-1,3,4-thiadiazino-[6,5-b(and 5,6-b)]-0 quinoline.

In the above process useful thioaroyl arylhydrazines

are illustrated by the following tabulation. Illustrative examples of $Ar^1$ are:

| | |
|---|---|
| 4-Nitrophenyl | 2-Pyrazinyl |
| 4-Diethylaminophenyl | 4-Pyridazinyl |
| 4-Nitro-1-naphthyl | 2-Methylthio-4-pyrimidinyl |
| 3-Pyridinyl | 3-Indolyl |
| 7-Chloro-4-quinolinyl | 2-Methyl-5-benzothiazolyl |
| 6-Quinolinyl | 2-Furyl |
| 7-Methoxy-4-isoquinolinyl | 2-Thienyl |
| 4-Methylmercaptophenyl | 2-Pyrrolyl |
| 2-Hydroxyphenyl | 4-Bromophenyl |
| 1-Naphthyl | |

Illustrative examples of $Ar^2$ are:

| | |
|---|---|
| 4-Dimethylsulfonamido-phenyl | 6-Chloro-4-isoquinolinyl |
| 2,4-dichloro-1-naphthyl | 2-Methyl-5-benzothiazolyl |
| 5-Chloro-3-pyridinyl | 4-Hydroxy-6-methyl-2-methylthio-5-pyrimidinyl |
| 6-Quinolinyl | 1-Methyl-4-indolinyl |
| 2-Cyanophenyl | 4-Diethylaminophenyl |

| -continued | |
|---|---|
| 3-Diethylaminophenyl | 4-Nitrophenyl |
| 4-Acetylaminophenyl | |
| 2-Hydroxyphenyl | 2,4-Dinitrophenyl |
| | 4-Methylsulfonylphenyl |

Further examples of vicinal halo or halonitro heterocycles include:
2-Chloro-3,5-dinitropyridine
4-nitro-2,4,6-trichloropyrimidine
Pentafluoropyridine
Tetrachloropyrazine
2,3-dichloro-5,6-dicarbomethoxypyrazine
2-Chloro-3-nitroquinoline Compounds obtained from the above include the following compounds (and/or their isomers).

a. 4-(2,4-Dichloro-1-naphthyl)-7-nitro-2-(6-quinolinyl)-4H-pyrido [2,3-e][1,3,4]thiadiazine
b. 4-(5-Chloro-3-pyridyl)-6,8-dichloro-2-(2-methylthio-4-pyrimidinyl-(4H-pyrimidino [5,4-e][1,3,4]thiadiazine
c. 4-(1-Methyl-4-indolyl)-2-(2-thienyl)-6,7,8-trifluoro-4H-pyridino [2,3-e][1,3,4]thiadiazine
d. 4-(6-Chloro-4-isoquinolinyl)-2-(2-furyl)-4H-quinolino-[2,3-e][1,3,4]thiadiazine
e. 7,8-Dichloro-4-(4-diethylaminophenyl)-2-(2-pyrrolyl)4H-pyridazino[3,4-e][1,3,4]thiadiazine
f. 6,7-Dicarbomethoxy-4(4-hydroxy-6-methyl-2-methylthio-5-pyrimidinyl)-2-(2-methyl-5-benzothiazolyl)-4H-pyrazino[2,3-e][1,3,4]thiadiazine The new thiadiazines of this invention are yellow, orange or red in color and are excellent lightfast dyes, particularly for polyester fabrics. The depth of dye color on the fabric is unexpectedly deeper than the spectral characteristics as the individual compounds indicate.

To illustrate the use of the thiadiazines of the invention as dyes, each dye compound listed in Table I was converted into a commercially usable form by milling the crude dye (e.g. 10 parts on a 100% basis) with about 2.5 parts of a lignin sulfonate dispersant and water in a colloid or sandmill. Milling was continued until a fine stable, aqueous dispersion or paste was obtained with dye particle size reduced to approximately one micron. The resultant dye dispersions were then applied to polyester fabric by an aqueous-pressure procedure as follows:

Five grams of commercially available "Dacron" 54 polyester fabric were put into an autoclave containing:

| | |
|---|---|
| An aqueous dye paste (15% active ingredient) containing each dye described in Table I | 0.1 gram |
| "Avitone" T sodium hydrocarbon sulfonate (10% solution) | 1.0 ml. |
| "Merpol" HCS long-chain alcohol-ethylene oxide adduct (10% solution) | 0.5 ml. |
| ethylenediaminetetraacetic acid, sodium salt (1% solution) | 1.25 ml. |
| butyl benzoate carrier (10% emulsion) | 1.5 ml. |
| water | to 75 ml. |

| -continued | |
|---|---|
| acetic acid | to adjust the pH to 5.5. |

The temperature was raised to 130° C. for 1 hour to effect dyeing. The dyed fabric was rinsed in water and then dried.

All of the 2,4-diarylquinoxalinothiadiazine dyes in Table I provided bright, fluorescent, greenish-yellow to reddish-yellow shades of excellent lightfastness on polyester. In general, the dyes exhibited good transfer, buildup and hydrolytic stability and had satisfactory sublimation fastness. Preferred dyes are those described in Examples 6, 31 and 35.

The compounds shown in Table I were prepared by reacting the appropriate thiobenzoylarylhydrazine shown in formula II with the appropriate 2,3-dichloroquinoxaline of formula III. In Table I, only $R^1$, $R^2$ and $R^3$ have been shown.

The products of Examples 6, 21, 23, 24 and 26 are assumed to be the 7- and/or 8-position isomers. The names and reactants are shown in Table II.

The thiobenzoylarylhydrazine reactants were prepared by thioaroylation of the appropriate arylhydrazines with a thioaroyl mercapto acetic acid (e.g. $Ar^1CSSCH_2COOH$) as described earlier in the specification.

The 6-sulfonyl and 6-sulfamyl-2,3-dichloroquinoxalines used in Examples 28–35 were prepared by chlorosulfonation of 2,3-dihydroxyquinoxaline, followed by chlorination with $PCl_3$-$POCl_3$ to form 6-chlorosulfonyl-2,3-dichloroquinoxaline. Reaction with the appropriate alcohol or amine provided the respective sulfonyl or sulfamyl 2,3-dichloroquinoxalines.

The 6-carbamyl-2, 3-dichloroquinoxalines used in Examples 23 and 27 were prepared by phosgenation of 6-carboxy-2,3-dihydroxyquinoxaline to provide 6-chlorocarbonyl-2,3-dichloroquinoxaline which, when treated with the appropriate amine, gave the 6-carbamyl-2,3- dichloroquinoxalines.

The 2,3-dichloroquinoxalines used in Examples 6, 21, 24 and 25 were prepared by the reaction of the appropriate 6- and/or 7-substituted o-phenylenediamine with oxalic acid to form the substituted 2,3-dihydroxyquinoxalines which were then phosgenated to provide the 2,3-dichloro compounds. For example, 2,3-dichloro-6-methylquinoxaline of Example 21 was prepared as follows:

A mixture of oxalic acid dihydrate (20 g), 3,4-toluenediamine ( 20 g), ethanol (60 ml), conc. hydrochloric acid (20 ml) and water (50 ml) was refluxed for 5 hours. After cooling to room temperature, the precipitate was removed by filtration, washed with water and dried to yield 27.1g of 2,3-dihydroxy-6-methylquinoxaline, mp >300° C. Phosgene was bubbled through a mixture of 27.1 g of the 2,3-dihydroxy compound in 200 ml of p-xylene and 5 ml of DMF at 120° C. The solution was degassed with nitrogen, clarified and the solvent flash evaporated to yield 26.2 g of 2,3-dichloro-6-methylquinoxaline, mp 112°–115° C.

TABLE I

| Example No. | $R^1$ | $R^2$ | $R^3$ | $\lambda_{max}$ (m$\mu$) | $a_{max}$ (liters g$^{-1}$cm$^{-1}$) | mp (° C) | Microanalysis Calcd. C | H | N | Found C | H | N | Shade on* Polyester |
|---|---|---|---|---|---|---|---|---|---|---|---|---|---|
| 10 | H | H | p-Cl | 415 | 29 | 234-5 | — | — | — | — | — | — | G-Y |
| 11 | H | H | m-Cl | 410 | 29 | 192-3 | — | — | — | — | — | — | G-Y |

TABLE I-continued

| Example No. | R¹ | R² | R³ | $\lambda_{max.}$ (m$\mu$) | $a_{max.}$ (liters g$^{-1}$cm$^{-1}$) | mp (° C) | Calcd. C | Calcd. H | Calcd. N | Found C | Found H | Found N | Shade on* Polyester |
|---|---|---|---|---|---|---|---|---|---|---|---|---|---|
| 12 | H | H | m-NO₂ | 410 | 27.1 | 151-4 | — | — | — | — | — | — | G-Y |
| 13 | H | H | o-CH₃ | 410 | 36.4 | 204-5 | 71.7 | 4.4 | 15.2 | 71.6 | 4.1 | 15.3 | G-Y |
| 14 | H | H | o-Cl | 405 | 31.6 | 183-5 | 64.9 | 3.3 | 14.4 | 64.1 | 3.1 | 14.3 | G-Y |
| 15 | H | H | p-Br | 415 | 27 | 238-9 | 58.2 | 3.0 | 12.9 | 57.8 | 3.0 | 12.8 | G-Y |
| 16 | H | H | m-Br | 412 | 27 | 194-6 | 58.2 | 3.0 | 12.9 | 58.0 | 2.8 | 12.9 | G-Y |
| 17 | H | H | o-OCH₃ | 410 | 33.1 | 179-181 | 68.8 | 4.2 | 14.6 | 68.0 | 3.9 | 14.5 | G-Y |
| 18 | H | H | o-Br | 405 | 29 | 202-4 | 58.2 | 3.0 | 12.9 | 57.5 | 2.7 | 12.8 | G-Y |
| 19 | H | H | p-CH₃ | 415 | 34.2 | 209-211 | 71.7 | 4.3 | 15.2 | 70.4 | 3.6 | 15.4 | G-Y |
| 20 | H | H | p-OCH₃ | 415 | 25.3 | 230-2 | — | — | — | — | — | — | G-Y |
| 21 | CH₃ | H | H | 417 | 34.3 | 187-9 | 71.7 | 4.3 | 15.2 | 72.2 | 4.7 | 15.3 | Y |
| 22 | H | H | m-CH₃ | 413 | 31.7 | 183-5 | 71.7 | 4.3 | 15.2 | 69.4 | 4.1 | 14.7 | G-Y |
| 23 | CH₃O(CH₂)₃NHCO— | H | H | 425 | 30.3 | 237 | 66.4 | 4.9 | 14.9 | 67.6 | 4.7 | 14.8 | Y |
| 24 | NO₂ | H | H | 454 | 45.3 | 248-53 | 63.2 | 3.3 | 17.5 | 62.0 | 3.2 | 17.2 | R-Y |
| 25 | CH₃ | CH₃ | H | 417 | 34.5 | 255-6 | — | — | — | — | — | — | Y |
| 26 | CH₃CH₂COO— | H | H | 428 | 35.6 | 214-5 | 67.8 | 4.5 | 13.2 | 67.2 | 4.0 | 13.2 | Y |
| 27 | (CH₃CH₂)₂NCO— | H | H | 420 | 28.1 | 125-6 | 68.9 | 5.1 | 15.5 | 68.5 | 5.2 | 15.6 | Y |
| 28 | (CH₃CH₂)₂NSO₂— | H | H | 425 | 29.5 | 186-7 | 61.4 | 4.7 | 14.3 | 62.5 | 4.7 | 14.6 | Y |
| 29 | (CH₃CH₂CH₂)₂NSO₂— | H | H | 425 | 26 | 187-9 | 62.7 | 5.3 | 13.5 | 62.0 | 5.1 | 13.4 | Y |
| 30 | O⟨⟩NSO₂— | H | H | 425 | 29.3 | 253-4 | 59.6 | 4.2 | 13.9 | 58.4 | 3.9 | 13.8 | Y |
| 31 | CH₃O(CH₂)₃NHSO₂— | H | H | 423 | 27.5 | 183-4 | 59.4 | 4.6 | 13.9 | 58.3 | 4.6 | 13.7 | Y |
| 32 | C₆H₅OSO₂— | H | H | 430 | 28.4 | 168-70 | — | — | — | — | — | — | R-Y |
| 33 | H₂NSO₂— | H | H | 425 | 31.8 | 310-12 | — | — | — | — | — | — | G-Y |
| 34 | CH₃CH₂NHSO₂— | H | H | 425 | 31 | 242-3 | — | — | — | — | — | — | G-Y |
| 35 | CH₃O(CH₂)₂O(CH₂)₃NHSO₂— | H | H | 423 | 26 | 111-4 | — | — | — | — | — | — | Y |

*G-Y = greenish-yellow; Y = yellow; R-Y = reddish-yellow.
$\lambda_{max.}$ = wave length of greatest absorption
$a_{max.}$ = dye absorptivity

TABLE II

| Example | Reactants | | Product QT = quinoxaline [2,3-e][1,3,4]thiadiazine |
|---|---|---|---|
| 10 | 2,3-dichloroquinoxaline | N-thiobenzoyl-N'-(4-chlorophenyl)hydrazine | 4-(4-chlorophenyl)-2-phenyl-4H-QT |
| 11 | 2,3-dichloroquinoxaline | N-thiobenzoyl-N'-(3-chlorophenyl)hydrazine | 4-(3-chlorophenyl)-2-phenyl-4H-QT |
| 12 | 2,3-dichloroquinoxaline | N-thiobenzoyl-N'-(3-nitrophenyl)hydrazine | 4-(3-nitrophenyl)-2-phenyl-4H-QT |
| 13 | 2,3-dichloroquinoxaline | N-thiobenzoyl-N'-(2-methylphenyl)hydrazine | 4-(2-methylphenyl)-2-phenyl-4H-QT |
| 14 | 2,3-dichloroquinoxaline | N-thiobenzoyl-N'-(2-chlorophenyl)hydrazine | 4-(2-chlorophenyl)-2-phenyl-4H-QT |
| 15 | 2,3-dichloroquinoxaline | N-thiobenzoyl-N'-(4-bromophenyl)hydrazine | 4-(4-bromophenyl)-2-phenyl-4H-QT |
| 16 | 2,3-dichloroquinoxaline | N-thiobenzoyl-N'-(3-bromophenyl)hydrazine | 4-(3-bromophenyl)-2-phenyl-4H-QT |
| 17 | 2,3-dichloroquinoxaline | N-thiobenzoyl-N'-(2-methoxyphenyl)hydrazine | 4-(2-methoxyphenyl)-2-phenyl-4H-QT |
| 18 | 2,3-dichloroquinoxaline | N-thiobenzoyl-N'-(2-bromophenyl)hydrazine | 4-(2-bromophenyl)-2-phenyl-4H-QT |
| 19 | 2,3-dichloroquinoxaline | N-thiobenzoyl-N'-(4-methylphenyl)hydrazine | 4-(4-methylphenyl)-2-phenyl-4H-QT |
| 20 | 2,3-dichloroquinoxaline | N-thiobenzoyl-N'-(4-methoxyphenyl)hydrazine | 4-(4-methoxyphenyl)-2-phenyl-4H-QT |

| Example | Reactants | | Product |
|---|---|---|---|
| 21 | 2,3-dichloro-6-methylquinoxaline | N-thiobenzoyl-N'-phenylhydrazine | 2,4-diphenyl-8-methyl-4H-QT |
| 22 | 2,3-dichloroquinoxaline | N-thiobenzoyl-N'-(3-methylphenyl)hydrazine | 4-(3-methylphenyl)-2-phenyl-4H-QT |
| 23 | 2,3-dichloro-6-(3-methoxypropyl carbamyl)quinoxaline | N-thiobenzoyl-N'-phenylhydrazine | 2,4-diphenyl-8-(3-methoxypropyl carbamyl)-4H-QT |
| 24 | 2,3-dichloro-6-nitroquinoxaline | N-thiobenzoyl-N'-phenylhydrazine | 2,4-diphenyl-8-nitro-4H-QT |
| 25 | 2,3-dichloro-6,7-dimethylquinoxaline | N-thiobenzoyl-N'-phenylhydrazine | 7,8-dimethyl-2,4-diphenyl-4H-QT |
| 26 | 2,3-dichloro-6-propionyloxyquinoxaline | N-thiobenzoyl-N'-phenylhydrazine | 2,4-diphenyl-8-propionyloxy-4H-QT |
| 27 | 2,3-dichloro-6-(N,N-diethyl carbamyl)quinoxaline | N-thiobenzoyl-N'-phenylhydrazine | 8-(N,N-diethyl carbamyl)-2,4-diphenyl-4H-QT |
| 28 | 2,3-dichloro-6-(N,N-diethyl sulfamyl)quinoxaline | N-thiobenzoyl-N'-phenylhydrazine | 8-(N,N-diethylsulfamyl)-2,4-diphenyl-4H-QT |
| 29 | 2,3-dichloro-6-(N,N-dipropylsulfamyl)quinoxaline | N-thiobenzoyl-N'-phenylhydrazine | 8-(N,N-dipropylsulfamyl)-2,4-diphenyl-4H-QT |
| 30 | 2,3-dichloro-6-morpholinosulfonylquinoxaline | N-thiobenzoyl-N'-phenylhydrazine | 8-morpholinosulfonyl-2,4-diphenyl-4H-QT |
| 31 | 2,3-dichloro-6-(3'-methoxypropylsulfamyl)quinoxaline | N-thiobenzoyl-N'-phenylhydrazine | 8-(3'-methoxypropylsulfamyl)-2,4-diphenyl-4H-QT |
| 32 | 2,3-dichloro-6-phenoxysulfonylquinoxaline | N-thiobenzoyl-N'-phenylhydrazine | 8-phenoxysulfonyl-2,4-diphenyl-4H-QT |
| 33 | 2,3-dichloro-6-sulfamyl- | N-thiobenzoyl-N'-phenyl- | 2,4-diphenyl-8-sulfamyl-4H-QT |

TABLE II-continued

| | quinoxaline | hydrazine | |
|---|---|---|---|
| 34 | 2,3-dichloro-6-(N-ethyl-sulfamyl)quinoxaline | N-thiobenzoyl-N'-phenyl-hydrazine | 8-(N-ethylsulfamyl)-2,4-diphenyl-4H-QT |
| 35 | 2,3-dichloro-6-(N-methoxy-ethoxypropylsulfamyl)quin-oxaline | N-thiobenzoyl-N'-phenyl-hydrazine | 8-(N-methoxyethoxypropylsulfamyl)-2,4-diphenyl-4H-QT |

What is claimed is:

1. A compound of the formula:

wherein
- $Ar^1$ is a monovalent aromatic radical of up to 10 nuclear atoms selected from the group consisting of a 6–10 carbon aryl, pyridinyl, 3-methylpyridinyl, quinolinyl, isoquinolinyl, pyridazinyl, pyrimidinyl, furyl, thienyl, pyrrolyl, thiazolyl, oxazolyl, pyrazinyl, pyrazolyl, imidazolyl, indolyl and benzothiazolyl;
- $Ar^2$ is a monovalent aromatic radical selected from the group consisting of aryl of 6–10 carbon atoms, pyridazinyl, pyrimidinyl, pyrazinyl, furyl, pyrrolyl, thienyl, thiazolyl, oxazolyl, imidazolyl, indolyl, 3- or 4-pyridinyl, 3-, 4-, 5-, 6-, or 7-quinolinyl, 4-, 5-, 6-, 7-, 8-isoquinolinyl and 5-, 6-, or 7-benzothiazolyl;
- each of $Ar^1$ and Ar optionally having up to 2 substituents selected from the group consisting of chloro, bromo, cyano, nitro, methoxy, methylthio, hydroxy, dialkylamino, dialkylsulfonamido, alkanoylamino, and alkyl, where each carbon-containing substituent is up to 4 carbon atoms;
- X and Y are 1 to 2 nitrogen atoms and conversely, 3 to 2 carbon atoms, the latter having (1) up to 2 substituents which are selected from the group consisting of halogen, nitro, methoxy, methylthio, sulfonamido, cyano, carboxy, alkoxyalkylsulfamyl, alkoxyalkylcarbamyl, carbamyl, alkyl, carbalkoxy, phenyloxysulfonyl, (di)alkylcarbamyl, sulfamyl, sulfonyl, alkanoylamino, (di)alkylsulfamyl, and dialkylamino where each alkyl is from 1–4 carbon atoms, and (2) optionally a butadienyl radical or a butadienyl radical substituted with up to 2 of the aforesaid substituents attached to 2 adjacent carbon atoms.

2. The compound of claim 1 wherein $Ar^1$ is phenyl.

3. The compound of claim 1 wherein $Ar^2$ is wherein $R^3$ is —H, —Cl, —Br, —NO$_2$, —CH$_3$, or —OCH$_3$.

4. The compound of claim 1 wherein X and Y are 2 nitrogen atoms and 2 carbon atoms which are adjacent and have a butadienyl radical attached thereto substituted with $R^1$ and $R^2$ wherein $R^1$ is —H, —Cl, —NO$_2$ —CH$_3$, alkoxyalkylcarbamyl, carbalkoxy, (di)alkylcarbamyl, sulfamyl, (di)alkylsulfamyl, alkoxyalkylsulfamyl or phenyloxysulfonyl, where each alkyl is 1–4 carbon atoms, and
$R^2$ is —H or CH$_3$.

5. The compound of claim 1 having the formula:

wherein
- $R^1$ is —H, —Cl, —NO$_2$, —CH$_3$, alkoxyalkylcarbamyl, carbalkoxy, (di)alkylcarbamyl, sulfamyl, (di)alkylsulfamyl, alkoxyalkylsulfamyl or phenyloxysulfonyl, where each alkyl is from 1–4 carbon atoms;
- $R^2$ is —H or —CH$_3$ and
- $R^3$ is —H, —Cl, —Br, —NO$_2$, —CH$_3$ or —OCH$_3$.

6. The compound of claim 5, 8-chloro-2,4-diphenyl-4H-quinoxalino[2,3-e][1,3,4]thiadiazine.

7. The compound of claim 5, 8-(3'-methoxypropylsulfamyl)-2,4-diphenyl-4H-quinoxalino[2,3-e][1,3,4]-thiadiazine.

8. The compound of claim 5, 8-(N-methoxyethoxypropylsulfamyl)-2,4-diphenyl-4H-quinoxalino[2,3-e][1,3,4]-thiadiazine.

9. A process for preparing the compounds of claim 1, comprising: contacting and reacting in a non-reactive solvent substantially equimolar amounts of a thioaroyl arylhydrazine of the formula:

$$Ar^1CNHNHAr^2$$
$$\underset{S}{\|}$$

wherein $Ar^1$ and $Ar^2$ are as defined in claim 1 and a vicinal halo or halonitro heterocyclic compound of the formula:

wherein X and Y are as defined in claim 1.

10. The process of claim 9 wherein the reaction is conducted at a temperature in the range of about 20°–100° C.

11. The process of claim 10 wherein the nonreactive solvent is a nitrile, a (di)lower alkyl-substituted amide or a liquid aromatic hydrocarbon.

12. The process of claim 11 wherein a basic absorber compound is additionally added to remove at least most of the acid generated in the reaction.

13. The process of claim 10 wherein the thioaroyl arylhydrazine is

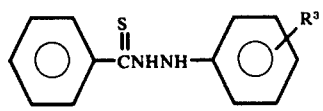

and the vicinal heterocyclic compound is a 2,3-dichloroquinoxaline of the formula:

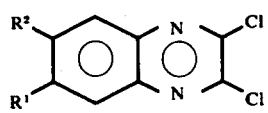

wherein $R^1$, $R^2$ and $R^3$ are as defined in claim 5.

14. The process of claim 13 wherein the non-reactive solvent is nitrile, a (di)lower alkyl-substituted amide or a liquid aromatic hydrocarbon and a basic absorber compound is additionally added to remove at least most of the acid generated in the reaction.

15. The process of claim 14 wherein the solvent is acetonitrile, propionitrile, dimethylformamide, xylene or toluene and the basic absorber compound is a lower alkyl tertiary amine.

* * * * *

UNITED STATES PATENT OFFICE
CERTIFICATE OF CORRECTION

PATENT NO. : 4,025,510
DATED : May 24, 1977
INVENTOR(S) : Arthur John Elliott

It is certified that error appears in the above-identified patent and that said Letters Patent are hereby corrected as shown below:

In column 10, line 12, the word "equivalnet" should read --equivalent--.

In column 10, line 34, between the chemical formulas, insert the words --or its isomer--.

In column 11, line 20, the partial chemical formula "-4-pyrimidinyl-(4H-pyrimidino" should read -- -4-pyrimidinyl)-4H-pyrimidino--.

Signed and Sealed this

Fifteenth Day of November 1977

[SEAL]

Attest:

RUTH C. MASON
Attesting Officer

LUTRELLE F. PARKER
Acting Commissioner of Patents and Trademarks